(12) United States Patent
Gross

(10) Patent No.: US 12,057,195 B2
(45) Date of Patent: Aug. 6, 2024

(54) SYSTEM AND METHOD FOR REAL-TIME PRIORITIZATION OF SEQUENCING

(71) Applicant: KONINKLIJKE PHILIPS N.V., Eindhoven (NL)

(72) Inventor: Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1318 days.

(21) Appl. No.: 16/603,255

(22) PCT Filed: Apr. 16, 2018

(86) PCT No.: PCT/EP2018/059626
§ 371 (c)(1),
(2) Date: Oct. 7, 2019

(87) PCT Pub. No.: WO2018/197245
PCT Pub. Date: Nov. 1, 2018

(65) Prior Publication Data
US 2020/0043569 A1    Feb. 6, 2020

Related U.S. Application Data

(60) Provisional application No. 62/608,987, filed on Dec. 21, 2017, provisional application No. 62/490,734, filed on Apr. 27, 2017.

(51) Int. Cl.
*G16B 30/00* (2019.01)
*C12Q 1/6869* (2018.01)
*G16B 50/00* (2019.01)
*G16B 50/30* (2019.01)

(52) U.S. Cl.
CPC ........... *G16B 30/00* (2019.02); *C12Q 1/6869* (2013.01); *G16B 50/00* (2019.02); *G16B 50/30* (2019.02)

(58) Field of Classification Search
CPC ........ G16B 30/00; G16B 50/00; G16B 50/30; G16B 30/10; C12Q 1/6869
See application file for complete search history.

(56) References Cited

U.S. PATENT DOCUMENTS

| | | |
|---|---|---|
| 7,670,553 B2 | 3/2010 | Babson |
| 9,968,901 B2 | 5/2018 | Head et al. |
| 2012/0208706 A1 | 8/2012 | Downing et al. |
| 2015/0119261 A1* | 4/2015 | Richard ............... C12Q 1/6806 |
| | | 506/26 |
| 2016/0333402 A1 | 11/2016 | Koller et al. |
| 2017/0121764 A1* | 5/2017 | Turner ................ C12N 9/1252 |
| 2017/0145502 A1* | 5/2017 | Shen ...................... C07H 19/10 |
| 2018/0127745 A1 | 5/2018 | Konermann et al. |
| 2018/0237950 A1 | 8/2018 | Brown et al. |

OTHER PUBLICATIONS

Van Dijk et al. "The Third Revolution in Sequencing Technology." Trend in Genetics, vol. 34, No. 9, pp. 666-681. (Year: 2018).*
Eid et al. "Real-Time DNA Sequencing from Single Polymerase Molecules." Science, vol. 323, pp. 133-138. (Year: 2009).*
Jain et al. "Improved data analysis for the MinION nanopore sequencer." Nature Methods, vol. 12, pp. 351-356. (Year: 2015).*
Loose et al. "Real-time selective sequencing using nanopore technology." Nature Methods, vol. 13, No. 9, pp. 751-754; and Online Methods, pp. 1-3. (Year: 2016).*
Farias-Hesson, E. et al., "Semi-Automated Library Preparation for High-Throughput DNA Sequencing Platforms", Journal of Biomedicine and Biotechnology, vol. 16, No. 3, Jan. 1, 2010, pp. 1-8.
Shearer, A.E. et al., "Solution-based targeted genomic enrichment for precious DNA samples", BMC Biotechnology, Biomed Central Ltd. London, GB, vol. 12, o. 1, May 4, 2012, p. 20.

* cited by examiner

*Primary Examiner* — John S Brusca
*Assistant Examiner* — Steven W. Bailey

(57) ABSTRACT

A method for prioritizing sequencing of nucleic acid molecules from two or more sources, comprising: (i) ligating one or more ends of each of a plurality of nucleic acid molecules to an adapter, wherein the adaptor is unique to each source and comprises a unique identifier nucleic acid sequence; (ii) pooling the nucleic acid molecules from each of the two or more sources; (iii) sequencing a plurality of nucleotides of an identifier nucleic acid sequence of an adapter; (iv) determining in real-time from which of the two or more sources the nucleic acid molecule being sequenced came; (v) determining, from a prioritization rule set and based on the determined source, a sequencing priority for the nucleic acid molecule; and (vi) allowing the sequencing process to proceed, or modifying the sequencing process, based on the determined sequencing priority.

15 Claims, 2 Drawing Sheets

SYSTEM AND METHOD FOR REAL-TIME PRIORITIZATION OF SEQUENCING

CROSS-REFERENCE TO PRIOR APPLICATIONS

This application is the U.S. National Phase application under 35 U.S.C. § 371 of International Application No. PCT/EP2018/059626, filed on Apr. 16, 2018, which claims the benefit of U.S. Patent Application No. 62/608,987, filed on Dec. 21, 2017 and U.S. Patent Application No. 62/490,734, filed on Apr. 27, 2017. These applications are hereby incorporated by reference herein.

FIELD OF THE INVENTION

The present disclosure is directed generally to methods and systems for real-time prioritization of sequencing of nucleic acid molecules from a pool comprising nucleic acid molecules from two or more sources.

BACKGROUND

Although recent innovations have greatly increased the speed of nucleic acid sequencing, it remains a costly and lengthy process. The cost and time required for pathogen-based sequencing, for example, can impact the clinical utility of the sequencing since complex therapy decisions must be made quickly.

For example, traditional microbiological laboratory procedures typically result in a definitive pathogen identification and antibiotic susceptibility, if the pathogen is bacterial, within several days after sample acquisition from the patient. In many cases the therapy decision initiated by the care team, made before definitive identification, is not optimally matched to the clinical susceptibility of the pathogen. Secondary issues can arise such as destruction of the host microbiome leading to secondary pathogen infections. On the other hand, ineffective therapy resulting from therapy initiated before definitive identification can result in further compromise or death of the patient.

Pathogen identification and antibiotic susceptibility analysis using next-generation sequencing techniques is an attractive and promising technology that could produce actionable results within a significantly shorter timeframe. However, sample preparation and sequencing speed currently prevents the use of next-generation sequencing in this way. Current approaches to remedy these deficiencies are to multiplex samples through the sequencing technology, which may reduce cost, but this can increase the time between sample acquisition and pathogen identification.

SUMMARY OF THE INVENTION

There is a continued need for prioritizing, in real-time, sequencing of a nucleic acid sequence within a pool of nucleic acid sequences from a plurality of sources.

The present disclosure is directed to inventive methods and systems for real-time prioritization of sequencing of nucleic acid molecules. Various embodiments and implementations herein are directed to a system including a sequencer comprising sequencing termination and/or prioritization capabilities, and a prioritization supervisor configured to prioritize sequencing within a pool of nucleic acid molecules from a plurality of sources, where the nucleic acid sequences from each source are labeled with a unique identifier. The sequencer analyzes the unique identifier and the prioritization supervisor determines a priority for the corresponding source in real-time from a predefined rule set. Based on the priority, the sequencer can prioritize the sequencing by, for example, allowing the sequencing to continue, by pausing sequencing, or by terminating the sequencing.

Generally in one aspect, a method for prioritizing sequencing of nucleic acid molecules from two or more sources is provided. The method includes the steps of: (i) ligating one or more ends of each of a plurality of nucleic acid molecules to an adapter, where nucleic acid molecules from each source are ligated to an adaptor unique to each source, each adaptor comprising a unique identifier nucleic acid sequence; (ii) pooling the ligated plurality of nucleic acid molecules from each of the two or more sources into a pool of nucleic acid molecules; (iii) sequencing, from the pool of nucleic acid molecules using a real-time single-molecule sequencing process, a plurality of nucleotides of an identifier nucleic acid sequence of an adapter; (iv) determining, in real-time from the sequenced plurality of nucleotides, from which of the two or more sources the nucleic acid molecule being sequenced came; (v) determining, from a prioritization rule set and based on the determined source of the nucleic acid molecule being sequenced, a sequencing priority for the nucleic acid molecule being sequenced; and (vi) allowing the real-time single-molecule sequencing process to proceed based on the determined sequencing priority, or modifying the real-time single-molecule sequencing process based on the determined sequencing priority.

According to an embodiment, the method further includes the step of fragmenting each of the plurality of nucleic acid samples into a plurality of fragmented nucleic acid molecule.

According to an embodiment, the method further includes the step of generating a prioritization rule set.

According to an embodiment, modifying the real-time single-molecule sequencing process comprises aborting the sequencing of the nucleic acid molecule being sequenced, ejecting the nucleic acid molecule being sequenced, or redirecting the nucleic acid molecule being sequenced.

According to an embodiment, the pool of nucleic acid molecules comprises nucleic acid molecules from a plurality of different sources.

According to an embodiment, the method further includes the step of receiving additional information about one or more of the two or more sources, and the determined sequencing priority is based at least in part on the received additional information.

According to an embodiment, the method further includes the step of adding nucleic acid molecules to the pool of nucleic acid molecules.

According to an embodiment, the sequencing priority is based at least in part on a user-defined priority for one or more of the two or more sources of nucleic acid molecules.

According to another aspect is a system for prioritizing sequencing of nucleic acid molecules in a pool of nucleic acid molecules from two or more sources, where the nucleic acid molecules from each source are ligated to a unique identifier nucleic acid sequence. The system includes a database of the unique identifier nucleic acid sequences, where each of the unique identifier nucleic acid sequences is associated with a respective source; a prioritization rule set comprising one or more rules for determining a sequencing priority for nucleic acid molecules from the two or more sources; and a priority supervisor configured to: (i) determine, in real-time from a sequenced plurality of nucleotides of an identifier nucleic acid sequence of an adapter, from which of the two or more sources a nucleic acid molecule being sequenced came; (ii) determine, based at least in part on the prioritization rule set and the determined source of the nucleic acid molecule being sequenced, a sequencing priority for the nucleic acid molecule being sequenced; and (iii) provide instructions to the real-time single-molecule sequencing process, based on the determined sequencing priority, to allow the process to proceed or to modify the process.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Figure 1:
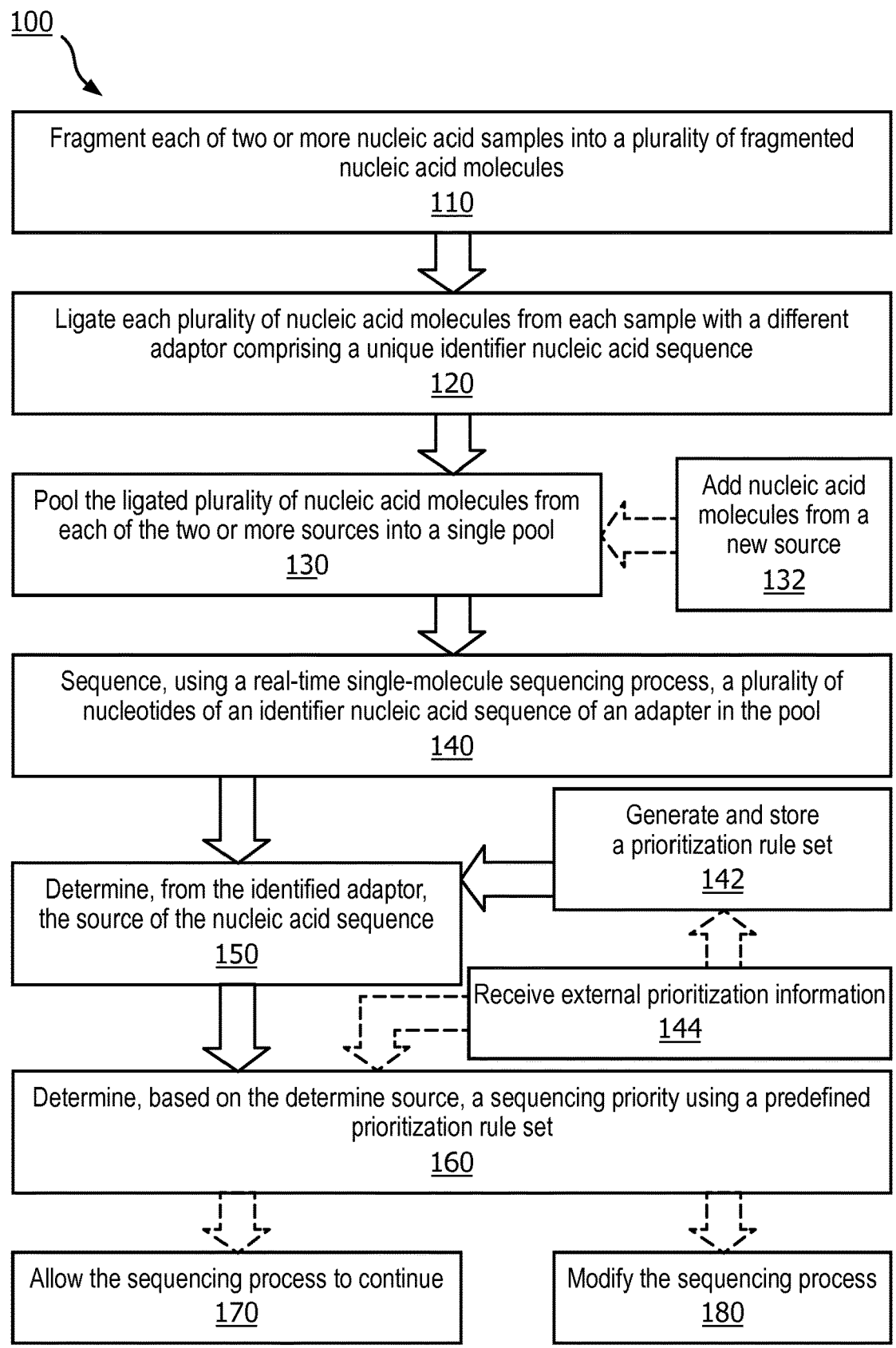
FIG. 1 is a flowchart of a method for prioritizing sequencing of nucleic acid molecules in real-time from a pool of nucleic acid molecules from different sources, in accordance with an embodiment.

The present disclosure describes various embodiments of a system and method for prioritizing sequencing of nucleic acid molecules in real-time from a pool of nucleic acid molecules from different sources. More generally, Applicant has recognized and appreciated that it would be beneficial to provide a system that enables selective sequencing. The system comprises a sequencer with sequencing termination and/or prioritization capabilities, and a prioritization supervisor configured to prioritize sequencing within a pool of nucleic acid molecules from a plurality of sources, where the nucleic acid sequences from each source are labeled with a unique identifier. The sequencer analyzes the unique identifier and the prioritization supervisor determines a priority for the corresponding source in real-time from a predefined rule set. Based on the priority, the sequencer can prioritize the sequencing by, for example, allowing the sequencing to continue, by pausing sequencing, or by terminating the sequencing Referring to FIG. 1, in one embodiment, is a flowchart of a method 100 for prioritizing sequencing of nucleic acid molecules in real-time from a pool of nucleic acid molecules from different sources.

At step 110 of the method, which may be optional, nucleic acid samples from two or more different sources are each fragmented to produce a plurality of fragmented nucleic acid molecules. The samples may comprise nucleic acid from one or more microorganisms such as bacteria, viruses, fungi, and/or from plants or animals, among other sources.

A sample may comprise nucleic acid molecules from one organism or from multiple organisms. As just one example, samples comprising nucleic acid may be collected from different patients for analysis. As another example, different samples comprising nucleic acid may be collected from the same object, surface, or organism. Samples may be obtained from a patient's wound, blood, catheter, urine, mouth, and/or stool, among many other possibilities and combinations.

Once obtained, a nucleic acid sample may be prepared for fragmentation and/or any other analysis, such as ligation discussed herein, using any method for nucleic acid sample preparation. For example the nucleic acid may be extracted, purified, and/or amplified, among many other preparations or treatments.

The nucleic acid samples can be fragmented using any method for nucleic acid fragmentation, such as shearing, sonication, enzymatic fragmentation, and/or chemical fragmentation, among other methods. Acoustic shearing and hydrodynamic shearing are examples of shearing methods, and transposase is an example of an enzyme used for enzymatic fragmentation. The fragmentation may produce fragmented nucleic acid molecules having a predetermined size, a standard size, and/or a variable size, among many other options. According to an embodiment, if a commercial sequencing platform is used for analysis of the fragmented nucleic acid molecules, fragmentation may be accomplished using a protocol and/or materials provided by or for the commercial sequencing platform. Alternatively, any protocol and/or materials may be utilized to fragment the nucleic acid samples.

At step 120 of the method, the nucleic acid molecules are ligated to an adaptor comprising an identifier nucleic acid unique to the source of the molecules. If step 120 follows step 110, the nucleic acid molecules will be fragmented, otherwise the molecules may be non-fragmented. According to an embodiment, steps 110 and 120 of the method can be performed simultaneously.

According to an embodiment, the adaptor comprises a unique identifier nucleic acid sequence or other identifier that allows for identification of the adaptor, and thus enables identification of the nucleic acid sample and source associated with the unique identifier nucleic acid sequence. Accordingly, each sample and/or each source will comprise an adaptor that is unique to that sample and/or source. When a plurality of samples are present in a complex mixture or pool, every nucleic acid molecule will be labeled with an adaptor that identifies the sample from which the molecule came, and optionally identifies the source of the sample. The identifier nucleic acid sequence of the adaptor may be associated in a database with any provided information.

Ligation can be accomplished by any method for ligating an adaptor to a nucleic acid molecule, such as enzymatic ligation. According to an embodiment, the nucleic acid molecules in the sample, fragmented or non-fragmented, are prepared for ligation. For example, the molecules may be repaired, A-tailed, or otherwise prepared for ligation.

According to an embodiment, the adaptor comprises or is attached to or is adjacent to a tether or other element that enables sequencing. For example, the tether or other element may align the nucleic acid molecule with a sequencing entrance, such as a pore, for sequencing. The adaptor may therefore be configured to adhere to or satisfy one or more requirements or restrictions of the selected sequencing platform.

At step 130 of the method, the ligated nucleic acid molecules from each of the two or more different sources are collected together into a single pool. For example, multiple samples from a single source and/or multiple samples from multiple sources may be combined in a sequencing pool such as a sample chamber of a sequencing platform. Multiple samples may be pooled together all at once, or additional samples may be added periodically or continuously. For example, new samples may be added as they are collected. Samples can be pooled or added to the pool at any point, without clearing or removing an existing pool. The samples may comprise nucleic acid molecules from one organism or from multiple organisms.

At optional step 132 of the method, nucleic acid molecules from a new source can be added to an existing pool of nucleic acid molecules. Due to the unique labeling of each plurality of nucleic acid molecules, new samples can be added to the pool and can still be identifiably sequenced. As just one example, samples may be collected from patients in a clinical setting. One or more samples may be collected from a patient, and there may be one or more patients, creating a plurality of samples. The samples can then be pooled for sequencing. As new samples are collected from a patient, such as over a time course, or as new samples are collected from new patients, the new samples can be added to the existing pool or to a new pool of samples.

At step 130 of the method, the ligated nucleic acid molecules from each of the two or more different sources are collected together into a single pool. For example, multiple samples from a single source and/or multiple samples from multiple sources may be combined in a sequencing pool such as a sample chamber of a sequencing platform. Multiple samples may be pooled together all at once, or additional samples may be added periodically or continuously. For example, new samples may be added as they are collected. Samples can be pooled or added to the pool at any point, without clearing or removing an existing pool. The samples may comprise nucleic acid molecules from one organism or from multiple organisms.

At step 140 of the method, the sequencing platform sequences at least a portion of the unique identifier nucleic acid sequence of the adaptor, comprising a plurality of sequenced nucleotides. The sequencing platform can be any sequencing platform, including but not limited to any systems described or otherwise envisioned herein. For example, the sequencing platform can be a real-time single-molecule sequencing platform. Accordingly, the sequencing platform obtains and communicates sequencing information in real-time, which enables one or more downstream steps of the method. According to an embodiment, the tether or other element of the adaptor aligns the nucleic acid molecule with a sequencing entrance, such as a pore, for sequencing.

According to an embodiment the sequencing information, which may be raw data that is converted into a sequence, is communicated to or from the sequencing platform for analysis and identification of the unique identifier nucleic acid sequence of the adaptor and thus identification of the sample and/or source.

At step 142 of the method, a prioritization rule set is generated and stored. The prioritization rule set may be generated by a user, or may be generated by an algorithm based on one or more user-defined priorities. Sequencing prioritization may be based on one or more priorities, and may be based on thresholds and/or a priority continuum. The user or the system may define priorities based on a purpose or use of the sequencing results. As another example, the user or the system may define priorities based on a source of the sample such as an identity of the patient and/or a location where the sample was obtained. The prioritization rule set may be stored in a memory or database of the sequencing platform, in the memory or database of a priority supervisor or module, or in any other a memory or database.

As an example, sequencing within a clinical setting may require multiple priority levels for samples. A patient with a serious or worsening condition, such as an infection by an unidentified pathogen, in addition to many other possible situations, may be at a highest priority level. A sample obtained for an epidemiological investigation or other routine check may be at a second priority level lower than the highest priority level. A sample obtained for environmental surveillance or other types of surveillance may be at a third priority level lower than the second priority level. A non-clinical sample may be at a fourth priority level lower than the third priority level. There may be additional priority levels below the fourth priority level, or intermediate between any of these priority levels. Additionally, any of these conditions may be assigned a higher or lower priority based on the settings of the system and/or on the needs of the user.

According to an embodiment, user or the system may define priorities based on the plurality of samples in the pool, and/or on the nucleic acid molecules that are currently being read by the platform. For example, the sequencing platform and/or a priority supervisor or module compares the status of the sample to the relative priority of the nucleic acid molecules actively being read by the sequencing platform. As described below, the priority supervisor or module utilizes this information to instruct the platform to instruct the sequencer to move the current strand elsewhere such as to waste or to a priority stage, or to terminate sequencing and free the sequencing pore for a higher priority molecule. For example, according to a possible prioritization rule, if 80% of the current sequencer subsystem reads are samples designated by the rule set as high priority, yet high priority samples are still not at acceptable quantity and/or quality, abort to the appropriate priority stagers if the current sample priority is not higher than a second priority level, else continue read. Many other rules and algorithms for determining when to continue a current read based on its priority, the status of other ongoing strand reads, the status of sequencing, and/or other variables are possible. In some embodiments, a machine learning trained model may be applied to make priority determinations.

Sequencing prioritization may be modified at any point before and during sequencing. For example, a user may add a new sample to the pool that has a priority level that exceeds the priority level of all current samples in the pool. The user may determine that an assigned or determined priority level for a sample in the pool is no longer necessary or appropriate, and can modify the assigned or determined priority level. For example, once the nucleic acid molecules within a sample have been sufficiently identified and/or otherwise characterized, the remaining nucleic acid molecules from that sample may no longer be necessary and may be relegated to the lowest priority. As another example, the condition of a patient that has provided one or more samples may worsen and the nucleic acid molecules from those samples may be assigned a higher priority.

According to an embodiment, the system comprises a memory or database storing the unique identifier nucleic acid sequences of the adaptors used by the system. For each defined identifier nucleic acid sequence there is a linker, pointer, or other association between that sequence and the source of the sample. Accordingly, when the unique identifier nucleic acid sequence is identified by sequencing, that identification will also comprise the source of the nucleic acid sample.

At optional step 144 of the method, the system receives external information that is utilized to generate or modify a prioritization rule set, and/or is otherwise used to determine or modify a sequencing priority. The information may be pushed to the system by a user or another computer, or the information may be periodically or continuously requested or otherwise queried by the sequencing platform or the priority supervisor.

For example, as discussed herein, the system may receive information within a clinical setting that is utilized to build or modify a prioritization rule set or to determine or modify a sequencing priority. The system receives or requests information about a patient associated with one or more samples currently being sequenced or is slated for sequencing, and determines from the received information that the patient's condition has changed and thus that the sequencing priority for the one or more samples associated with the patient should change or stay the same depending on the input. The system may receive this via manual input from a clinician, or it may receive it in response to a query to a medical records database, among other options. For example, if the system receives input indicating that a patient's condition has worsened and that the condition may benefit from the sequencing data, then the system may prioritize the patient's samples. Similarly, if the system receives input indicating that a patient's condition has stabilized, the system may lower the priority of the patient's samples. The change in priority may be dependent not only on the one patient's condition, but also on the condition of every patient with samples currently being analyzed or slated to be analyzed.

At step 150 of the method, the sequencing information from the sequencing platform is utilized to determine, in real-time, the identity of the unique identifier nucleic acid sequence being sequenced. Identification of the unique nucleic acid sequence also identifies adaptor and the corresponding sample and/or source. According to an embodiment, the unique identifier nucleic acid sequence being sequenced is identified by comparing the sequencing information from the sequencing platform to a table or database of identifier nucleic acid sequences. An identifier nucleic acid sequences may positively identified by matching a predetermined minimum number or percentage of nucleotides. The comparison may require a minimum number of nucleotides for a definitive identification, although this setting may be modified based on the needs of the system, the needs of the user, and/or the diversity of the identifier nucleic acid sequences.

At step 160 of the method, the system determines a sequencing priority for the nucleic acid molecule being read based on the determined identity of the nucleic acid molecule and the predefined rule set. Sequencing prioritization may be based on one or more priorities as described or otherwise envisioned herein.

The prioritization rule set may be stored in a memory or database of the sequencing platform, in the memory or database of a priority supervisor or module, or in any other a memory or database. When the system determines the identity of the nucleic acid molecule being read via the unique nucleic acid sequence of the adaptor, the system can query the memory or database comprising the prioritization rule set for a priority level.

Based on the obtained priority level from the prioritization rule set, the sequencing platform or the priority supervisor or module makes a sequencing decision. According to an embodiment, the sequencing platform carries out a sequencing decision at the command or control of the priority supervisor or module. As a result, the sequencing platform preferentially sequences nucleic acid molecules from the pool based on the priority rule set.

For example, at step 170 of the method, the determined priority level informs the sequencing platform and/or the priority supervisor or module to allow the current read to continue. Alternatively, at step 180 of the method, the determined priority level informs the sequencing platform and/or the priority supervisor or module to modify the current read process. Modification may include anything other than allowing the current read to continue. For example, modification may include aborting the read, redirecting the read to waste, ejecting the read, pausing the read, ignoring the read, and/or any other modification.

Figure 2:
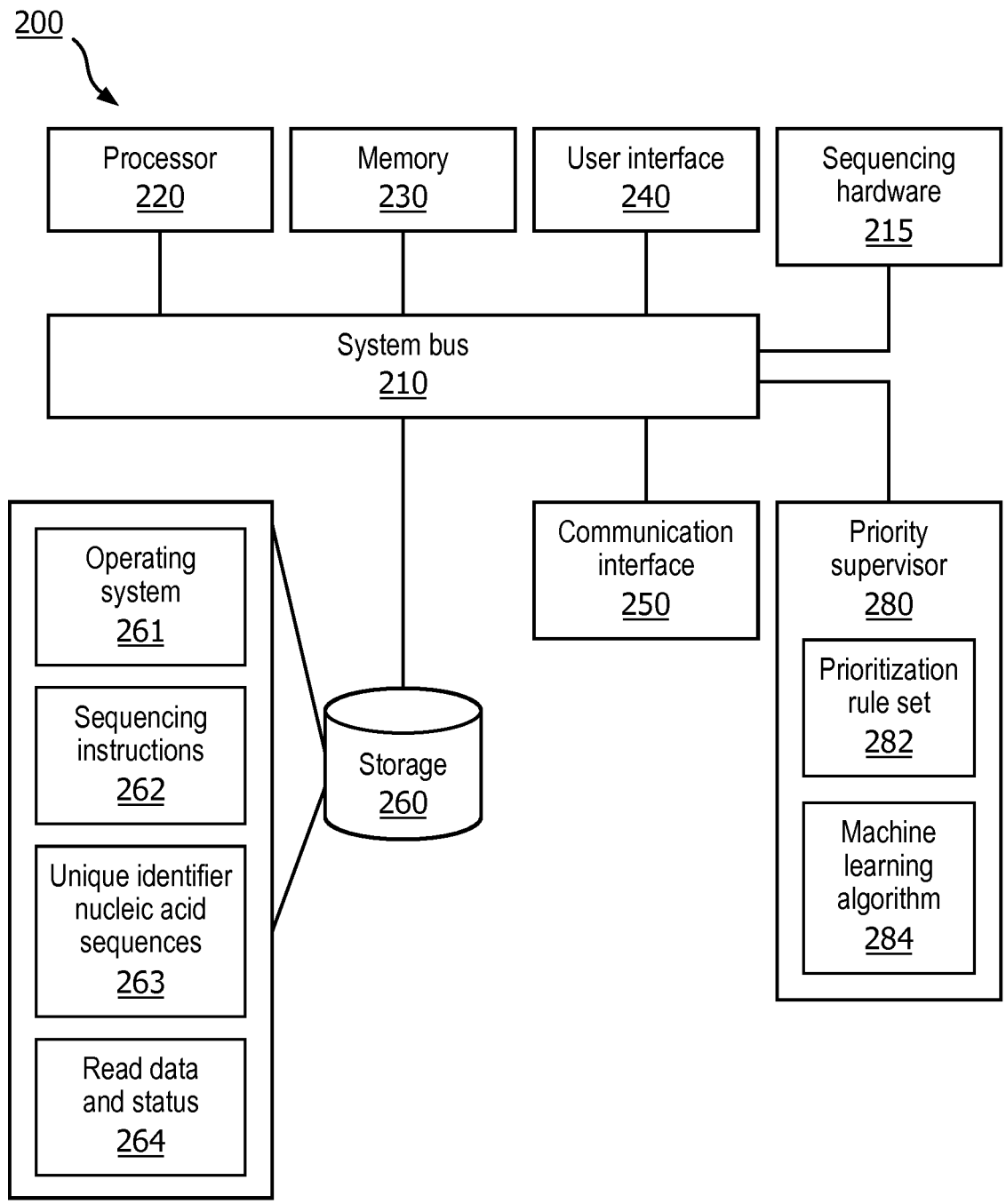
FIG. 2 is a schematic representation of a sequencing prioritization system, in accordance with an embodiment.

Referring to FIG. 2, in one embodiment, is an exemplary hardware diagram 200 for implementing a sequencer or sequencing platform, or a device for processing data received from a sequencer or sequencing platform. As shown, device 200 includes a processor 220, memory 230, user interface 240, communication interface 250, storage 260, and priority supervisor 280 interconnected via one or more system buses 210. In some embodiments, such as those where the system comprises or implements a sequencer or sequencing platform, the hardware may include additional sequencing hardware 215 such as a real-time single-molecule sequencer, including but not limited to a pore-based sequencer, although many other sequencing platforms are possible. It will be understood that FIG. 2 constitutes, in some respects, an abstraction and that the actual organization of the components of the device 200 may be different and more complex than illustrated.

According to an embodiment, system 200 comprises a processor 220 capable of executing instructions stored in memory 230 or storage 260 or otherwise processing data. Processor 220 performs one or more steps of the method, and may comprise one or more of the modules described or otherwise envisioned herein. Processor 220 may be formed of one or multiple modules, and can comprise, for example, a memory 230. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user such as an administrator. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of hardware 200. Where hardware 200 implements a sequencer and includes sequencing hardware 215, storage 260 may include sequencing instructions 262 for operating the sequencing hardware 215 and receiving commands from other software such as commands to eject a strand to waste or staging, reverse a strand, configure the pore matrix, reread a region, ignoring the read, and so on. Storage 260 may also store the unique identifier nucleic acid sequences 263 of the adaptors used by the system. For each defined identifier nucleic acid sequence 263 there is a linker, pointer, or other association between that sequence and the source of the sample. Storage 260 may also include read data and status information 264 for a read currently underway.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

Priority supervisor 280 comprises or stores a prioritization rule set 282 comprising one or more rules or priorities for determining a real-time sequencing priority for a nucleic acid molecule being read. Priority supervisor 280 determines an identification of, or receives information about an identification of, a nucleic acid molecule being read based on an identified adaptor. The priority supervisor then uses the prioritization rule set 282 to determine a sequencing priority for the nucleic acid molecule being read. The prioritization rule set may be dynamic and thus can determine a priority based on real-time conditions and/or needs of the user and/or the sequencing platform as described or otherwise envisioned herein. Based on the determined priority, priority supervisor 280 provides instructions (such as through an API, among other methods) to the sequencing platform such as continue read, move the molecule to waste or to a priority stage, or to terminate sequencing to free the reader for a higher priority molecule, among other possible instructions. According to some sequencing platforms, the priority supervisor 280 provides instructions to individual pores or other single-molecule readers based on the determined priority. Accordingly, where hardware 200 implements a sequencer and includes sequencing hardware 215, priority supervisor 280 may include sequencing instructions for operating the sequencing hardware 215.

Priority supervisor 280 may comprise or store a machine learning algorithm 284 configured to generate or modify a prioritization rule set 282 based in whole or in part on user input, user feedback, system feedback, training datasets, and/or other sources. For example, the machine learning algorithm 284 can be trained using a training dataset configured to train the machine learning algorithm 284 to learn which samples or sources should have a higher or lower priority either alone or compared to other samples or sources.

While host device 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where device 200 is implemented in a cloud computing system, the various hardware components may belong to separate physical systems. For example, processor 220 may include a first processor in a first server and a second processor in a second server. Many other variations and configurations are possible.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for prioritizing sequencing of nucleic acid molecules from two or more sources, comprising:
    ligating one or more ends of each of a plurality of nucleic acid molecules to an adapter, wherein nucleic acid molecules from each source are ligated to an adaptor unique to each source, each adaptor comprising a unique identifier nucleic acid sequence;
    pooling the ligated plurality of nucleic acid molecules from each of the two or more sources into a pool of nucleic acid molecules;
    sequencing, from the pool of nucleic acid molecules using a real-time single-molecule sequencing process, a plurality of nucleotides of an identifier nucleic acid sequence of an adapter;
    determining, in real-time from the sequenced plurality of nucleotides, from which of the two or more sources the nucleic acid molecule being sequenced came;
    determining, from a prioritization rule set and based on the determined source of the nucleic acid molecule being sequenced, a sequencing priority for the nucleic acid molecule being sequenced, wherein the prioritization rule set is modified based on information received regarding a health condition of a subject; and
    allowing the real-time single-molecule sequencing process to proceed based on the determined sequencing priority, or modifying (180) the real-time single-molecule sequencing process based on the determined sequencing priority.

2. The method of claim 1, further comprising the step of fragmenting each of the plurality of nucleic acid molecules into a plurality of fragmented nucleic acid molecule.

3. The method of claim 1, further comprising the step of generating a prioritization rule set.

4. The method of claim 1, wherein modifying the real-time single-molecule sequencing process comprises aborting the sequencing of the nucleic acid molecule being sequenced.

5. The method of claim 1, wherein modifying the real-time single-molecule sequencing process comprises ejecting the nucleic acid molecule being sequenced.

6. The method of claim 1, wherein modifying the real-time single-molecule sequencing process comprises redirecting the nucleic acid molecule being sequenced.

7. The method of claim 1, further comprising the step of receiving additional information about one or more of the two or more sources, wherein the determined sequencing priority is based at least in part on the received additional information.

8. The method of claim 1, further comprising the step of adding nucleic acid molecules to the pool of nucleic acid molecules.

9. The method of claim 1, wherein the sequencing priority is based at least in part on a user-defined priority for one or more of the two or more sources of nucleic acid molecules.

10. A system for prioritizing sequencing of nucleic acid molecules in a pool of nucleic acid molecules from two or more sources, wherein the nucleic acid molecules from each source are ligated to a unique identifier nucleic acid sequence, the system comprising:
    a database, stored in one or more computer readable storage devices, of the unique identifier nucleic acid sequences, wherein each of the unique identifier nucleic acid sequences is associated with a respective source;
a prioritization rule set, stored in the one or more computer readable storage devices, comprising one or more rules for determining a sequencing priority for nucleic acid molecules from the two or more sources, wherein the prioritization rule set is modified based on information received regarding a health condition of a subject; and
a priority supervisor configured to execute one or more program instructions stored on the one or more computer readable storage device using one or more computer processors, the one or more program instructions comprising: (i) program instructions to determine, in real-time from a sequenced plurality of nucleotides of an identifier nucleic acid sequence of an adapter, from which of the two or more sources a nucleic acid molecule being sequenced came; (ii) program instructions to determine, based at least in part on the prioritization rule set and the determined source of the nucleic acid molecule being sequenced, a sequencing priority for the nucleic acid molecule being sequenced; and (iii) program instructions to provide instructions to the real-time single-molecule sequencing process, based on the determined sequencing priority, to allow the process to proceed or to modify the process.

11. The system of claim 10, wherein modifying the real-time single-molecule sequencing process comprises program instructions to aborting the sequencing of the nucleic acid molecule being sequenced.

12. The system of claim 10, wherein modifying the real-time single-molecule sequencing process comprises program instructions to ejecting the nucleic acid molecule being sequenced.

13. The system of claim 10, wherein modifying the real-time single-molecule sequencing process comprises program instructions redirecting the nucleic acid molecule being sequenced.

14. The system of claim 10, wherein the pool of nucleic acid molecules comprises nucleic acid molecules from a plurality of different sources.

15. The system of claim 10, wherein the sequencing priority is based at least in part on a user-defined priority for one or more of the two or more sources of nucleic acid molecules.

* * * * *